(12) United States Patent
Asirvatham (10) Patent No.: US 7,696,294 B2
(45) Date of Patent: Apr. 13, 2010

(54) SILOXANE POLYMERS AND USES THEREOF

(75) Inventor: Edward T. Asirvatham, Chatham, NJ (US)

(73) Assignee: Honeywell International Inc., Morristown, NJ (US)

( * ) Notice: Subject to any disclaimer, the term of this patent is extended or adjusted under 35 U.S.C. 154(b) by 107 days.

(21) Appl. No.: 11/830,479

(22) Filed: Jul. 30, 2007

(65) Prior Publication Data

US 2008/0033119 A1  Feb. 7, 2008

Related U.S. Application Data (60) Provisional application No. 60/835,013, filed on Aug. 2, 2006.

(51) Int. Cl.
*C08G 77/04* (2006.01)
*C08G 77/12* (2006.01)

(52) U.S. Cl. .......................... 528/25; 528/31

(58) Field of Classification Search ........... 525/471
See application file for complete search history.

(56) References Cited

U.S. PATENT DOCUMENTS

| | | | |
|---|---|---|---|
| 2,803,637 A * | 8/1957 | Speier | 556/436 |
| 2,920,092 A * | 1/1960 | Bailey | 556/436 |
| 2,989,559 A * | 6/1961 | Marsden | 556/436 |
| 3,628,907 A * | 12/1971 | Fish | 8/120 |
| 3,928,644 A | 12/1975 | Schreiber et al. | |
| 5,021,601 A * | 6/1991 | Frances et al. | 556/436 |
| 5,468,477 A * | 11/1995 | Kumar et al. | 424/78.17 |
| 5,789,516 A * | 8/1998 | Graiver et al. | 528/19 |
| 6,630,133 B1 | 10/2003 | Dupuis | |
| 6,716,441 B1 | 4/2004 | Osborne et al. | |
| 6,903,208 B2 | 6/2005 | Findlay et al. | |
| 2002/0183473 A1* | 12/2002 | Matyjaszewski et al. | 526/335 |
| 2007/0129520 A1* | 6/2007 | Ochs et al. | 528/28 |
| 2008/0161500 A1* | 7/2008 | Stark et al. | 525/342 |
| 2008/0262149 A1* | 10/2008 | Osawa | 524/588 |
| 2009/0137764 A1* | 5/2009 | Sutton et al. | 528/25 |

FOREIGN PATENT DOCUMENTS

| | | |
|---|---|---|
| JP | 2007/227072 | 9/2007 |
| WO | 2005049697 A | 6/2005 |
| WO | 2006/014328 | 2/2006 |
| WO | 2006/014367 | 2/2006 |
| WO | WO2006122707 A | 11/2006 |

\* cited by examiner

*Primary Examiner*—Randy Gulakowski
*Assistant Examiner*—Robert Loewe
(74) *Attorney, Agent, or Firm*—Erika S. Wilson (57) ABSTRACT

A method for preparing a siloxane polymer comprising the steps of (a) providing an aldehyde-based redox initiator; and (b) reacting said redox initiator with a siloxane having a plurality of end-capped hydride moieties to form a siloxane polymer having a plurality of terminal aldehyde moieties.

32 Claims, 4 Drawing Sheets

Molar Mass (D)

Analytical Data

| Kn16/242 | Methacrylic ethyl ester, AFSo3 |
| --- | --- |
| | Experiment without chlorobenzene as solvent; mixture got solid |

FIG 4

SILOXANE POLYMERS AND USES THEREOF

CROSS REFERENCE TO RELATED APPLICATIONS

This application is related to, and claims the priority benefit of, Provisional U.S. Application No. 60/835,013, filed Aug. 2, 2006, which is incorporated herein by reference.

FIELD OF INVENTION

This invention relates generally to siloxane compositions. More specifically, this invention relates to methods of producing siloxane polymers having aldehyde functionality, as well as compositions and uses of the same.

BACKGROUND

Siloxane compounds constitute an important class of industrial chemicals that are commonly found in organic copolymers of various forms including fluids, gels, elastomers, and resins. By modifying a siloxane with certain organofunctional groups and then linking these compounds to form an organic polymer, compositions can be formed having a wide variety of desirable physical and chemical properties such as improved impact resistance, flame resistance, heat stability, lubricity, and flow properties. Many of these compounds have use in such diverse applications as wetting agents, manufacturing processing aides, surfactants, foam control additives, pressure sensitive adhesives, thermoplastic elastomers, compatibilizing agents, water repellant materials, dry cleaning fluids, textile aids, personal and household care, preservatives, pesticides, and electronic circuits. In addition, many of these polymers and copolymers are non-toxic and environmentally compatible and can effectively be used in cosmetic and personal care products. Examples of modified siloxanes include aryl-functional silicone (see, e.g., U.S. Pat. No. 6,716,441); silicone acrylates (see, e.g., U.S. Pat. No. 6,630,133); amino-, epoxy-, and anhydride-functional silicones (see, e.g., US 2003/0162688); and silicone-fluoroalkyl polyether (see, e.g., JP 2006 045102).

Of particular interest to the present invention is siloxane polymers having aldehyde functionality. Aldehyde functional siloxanes are reactive with several synthetic and natural compounds. For example, aldehyde functional groups can react with sugars, starches, sucrose esters, and cellulose to form acetal derivatives, and with proteins, amino acids, and peptides to form imine derivatives.

Aldehyde functional siloxanes, particularly siloxane polymers having terminal aldehyde functionality, can also be utilized as part of a multifunctional polymer or copolymer by either blending two or more types of reactive polymers or by forming a copolymer comprising the aldehyde functional siloxane. These multifunctional polymers, which can have properties that are not achievable from their individual polymer ingredients alone, are particularly useful in formulating personal care products. For example, siloxane polymers and multifunctional copolymers can suspend biologically and/or cosmetically active ingredients via encapsulation, etc., and deliver these active ingredients to the desired site of activation such as the skin, nails, or hair. Using a siloxane polymer in this way can minimize the concentration of active ingredients of a personal care product (e.g., via time release dosing), thus reducing adverse side effects such as irritation. In addition, such polymers and copolymers provide for rheological control, hydrophobicity, emolliency, pigment dispersion, good film forming properties, lubrication, adhesion, foam control, surface modification, cationic/anionic surfactant, and can also provide a product with a desirable tactile impression such as soft-silky feel. Multifunctional polymers may also provide a more economic means of producing certain personal care products, e.g., by reducing the number of formulations required for a particular product line.

Aldehyde-functional siloxanes, as well as polymer and copolymers derived therefrom, have been described in WO 2006/014328 and WO 2006/014367, both of which are assigned to the same assignee as the present application and both of which are incorporated herein by reference.

SUMMARY OF THE INVENTION

The Applicants have discovered a method of preparing functionalized siloxane wherein a redox initiator having a specific functionality is formed and then reacted with hydride end-capped siloxane to produce a siloxane polymer. Such polymers have a plurality of terminal functional groups, such as aldehydes, which produce better adhesion characteristics compared to bi-functional polymers. The improved adhesion is believed to result from the increased number of reactive sites on the polymer.

In addition, such siloxane polymers having aldehyde functionality can be reacted with other monomer or polymers having different reactive functional groups to form a multifunctional copolymer. Such copolymers can posses functionalities that are not achievable from the individual polymers.

Thus, according to one aspect of the invention, a method for preparing a siloxane polymer is provided comprising the steps of (a) providing a redox initiator having the formula:

wherein Z is an aldehyde having carboxyl and carbinol functionalities; X is an abstraction moiety; $R_1$ is a stabilizing constituent; and A is a $C_2$-$C_6$ alkene or a $C_2$-$C_6$ alkyne; and (b) reacting the redox initiator with a hydride end-capped siloxane to form a siloxane polymer having a plurality of terminal aldehyde moieties.

According to another aspect of the invention, provided is a method of producing a copolymers comprising the steps of (a) providing a siloxane polymer having aldehyde functionality according to the present invention; (b) providing a monomer or polymer having a vinyl functional group and a second functional group; and (c) reacting the siloxane polymer with the monomer or polymer to produce a copolymer having aldehyde functionality and the second functionality.

According to another aspect of the invention, provided is a siloxane polymer comprising a plurality of moieties having the structure:

wherein x' is an integer from 2 to 6; $R_1$ is methyl, ethyl, or phenyl; and $R_8$ is independently selected from the group consisting of hydrogen, $C_1$-$C_{50}$ straight or branched alkyl, $C_3$-$C_{12}$ substituted or unsubstituted cyclic, $C_1$-$C_{11}$ heterocyclic, $C_6$-$C_8$ aryl, $C_6$-$C_8$ aryloxy, $C_1$-$C_{12}$ alkoxy, $C_2$-$C_{12}$ dialkylamino, $C_1$-$C_{12}$ alkylthio, $C_1$-$C_{12}$ fluoroalkyl, $C_1$-$C_{12}$ epoxy, $C_1$-$C_6$ acrylic or methacryoxy, $C_6$-$C_{50}$ polyether, or some combination thereof.

According to another aspect of the invention, provided is a copolymer product comprising the siloxane polymer structure described above and a second monomer or polymer having a different structure.

According to another aspect of the invention, provided is a personal care product comprising at least one siloxane polymer according to the present invention.

According to yet another aspect of the invention, a method of delivering an active ingredient to a bodily surface is provided comprising the step of suspending the active ingredient in a siloxane polymer according to the present invention.

DETAILED DESCRIPTION OF THE INVENTION

Provided are methods for producing siloxane polymers that can be reacted with other monomers or polymers to form a multifunctional copolymer. The copolymerization site can be customized to efficiently produce a wide variety of block and graft copolymers.

The term "redox initiator", as used herein, refers to a system which effects the radical polymerization of the polymer. Specifically, a redox initiator, when attached to a siloxane, promotes oxidative coupling between the siloxane and one or more vinyl groups of a monomer or polymer to form block or graft siloxane copolymers. This process of oxidative coupling, which is also known in the art as "redox polymerization", generally involves the transfer of electrons between the redox initiator attached to the siloxane and at least one other monomer or polymer during the copolymerization reaction. Without being bound to any particular theory, it is believed that redox initiators suitable for the present invention accept an electron during a redox reaction, thereby creating a polymeric siloxane radical. This polymeric radical, in turn, reacts with vinylic monomers and/or polymers to form a siloxane-vinyl block or graft copolymer.

Several redox initiators are known in the art. Those suitable for use with the present invention comprise (1) a free radical initiator which serves to facilitate reduction of a polymeric siloxane, (2) an abstraction moiety which is removable from the redox initiator providing a pair of free electrons, (3) a tertiary alpha-carbon which functions as a copolymerization site, (4) a stabilizing constituent for controlling the copolymerization kinetics, and (5) a group capable of being hydrosilylated which serves to attach the redox initiator to the siloxane. Generally, redox initiators of the present invention will be of Formula (II):

wherein:
Z is an aldehyde, preferably having carbinol and carboxyl functionalities;
$C_{alpha}$ is the first carbon adjacent to Z;
X is an abstraction moiety;
$R_1$ is a stabilizing constituent; and
A is a group capable of being hydrosilylated, preferably alkene or alkyne.

With respect to the free radical initiator, Z, it is an agent used to start the redox copolymerization reaction involving the polymerizable siloxane. The redox initiator, when attached to the siloxane, must be reducable so as to readily form a polymeric free radical. This polymeric free radical has one unpaired electron that is produced upon the splitting of a molecular bond. That is, the free radical has at least one of the bonding orbitals occupied by a single electron. Once the polymeric radical is formed, it can then undergo oxidative coupling with another monomer and/or polymer. This action starts a chain reaction wherein the radicals that are consumed by the formation of a polymer or copolymer bond are regenerated, thereby leading to the formation of a polymer or copolymer.

With respect to the abstraction moeity, X, it is the moeity that leaves the molecule in order to create the polymeric free radical. Generally, the abstraction site becomes the location of polymeric linkage. According to the present invention, these abstraction moieties are a hydrogen or a highly electronegative atom, such as a halogen. Examples of preferred abstraction moieties include, but are not limited to, hydrogen, chlorine, bromine, and iodine.

With respect to the stabilizing constituent, $R_1$, it is a moiety that stabilizes the free radical formed during the polymerization reaction, preferably by resonance forces. It is known that more stable free radicals form more easily. That is, the ease at which radical formation occurs (i.e. the acceptance of an electron and corresponding abstraction of hydrogen or halogen) increases as the stability of the resulting free radical increases. The dissociation energy of the abstraction moeity bond generally provides a measurement of the relative inherent stability of the free radical. With respect to carbon-based free radicals, stability order is as follows:

Tertiary>Secondary>Primary>$CH_4$>Vinylic

Increasing the number of alkyl substituent on the radical center generally leads to an increase in stability, which is thought to be caused by hyperconjugation. Thus, redox initiators having a radical on a tertiary carbon (i.e. a carbon having only one abstraction moiety) are preferred to redox initiators having a radical on a secondary carbon because the the tertiary carbon-centered radical is more stable due to more distinct resonance stabilization. Such tertiary carbon-centered radicals are formed, for example, by $R_1$ being an alkyl or a phenyl. For the formation of siloxane polymers, preferred stabilizing constituents are methyl, ethyl, and phenyl, with phenyl being particularly preferred.

The stability of free radicals of the present invention is also enhanced by the presence at the radical center of either an electron-donating group or an electron withdrawing group. It is believed that this increased stability arises from the further increase in resonance. Examples of $R_1$ as an electron donating group include, but are not limited to, alkyloxy, aryloxy, thioethers, dialkyamines, or a phenyl substituted, preferably at the fourth carbon, with an alkyoxy, aryloxy, thioether, or dialkylamine. Particularly preferred alkyloxies include those having the formula —O—$R_2$, wherein $R_2$ is a $C_1$-$C_3$ alkyl. Particular preferred aryloxies include those having the formula —O—($C_6H_6$). Particularly preferred thioethers include those having the formula —S—$R_3$, wherein $R_3$ is a $C_1$-$C_3$ alkyl or a phenyl. Particular preferred dialkylamines include those having the formula —N($R_4$)$_2$, wherein $R_4$ is methyl, ethyl, or phenyl. Examples of $R_1$ as an electron withdrawing group include, but are not limited to aryls substituted, preferably at the fourth carbon, with nitro, nitrile, aldehyde, $C_1$-$C_3$ ketone, or $C_1$-$C_3$ ester.

The particular $R_1$ substituent incorporated into the redox initiator will depend on the desired reaction kinetics, which can easily be determined by those skilled in the art without undue experimentation. Thus, for copolymerization reactions requiring a decrease in speed and an increase in selectivity, a redox initiator is synthesized having a substituent capable of resonance stabilizing a free radical, such as aromatic rings. In contrast, for copolymerization reactions requiring an increase in speed and a decrease in selectivity, a redox initiator is synthesized with a group having less resonance stabilizing characteristics, such as methyl. The functionality of the $R_1$ substituent may also be considered in choosing a particular $R_1$.

Redox initiators having tertiary carbons are also preferred because polymerization occurs at the site of the hydrogen abstraction and, in the case of tertiary carbons, there is only one abstraction site. Restriction of the polymerization reaction to a single site reduces the uncontrollable side-chain reactions and the resulting undesired cross-linked polymers.

With respect to the group capable of being hydrosilylated, A, it is a functional moeity capable of bonding to a siloxane, preferably via a hydrosilylation reaction, although any chemical process known in the art may be used. Such a hydrosilylation reaction occurs at a silicon-hydrogen bond of a siloxane and involves the addition of the siloxane across the terminal carbon-carbon double bond or triple bond of the redox initiator. Thus, preferably A is an alkene or alkyne, and more preferably a $C_3$ alkene or alkyne having its double or triple bond, respectively, at a terminal end of the redox initiator distal to the aldehyde group.

Typically, the hydrosilylation process is carried out in the presence of a catalyst, such as platinum. In certain preferred embodiments, the redox initiator bearing the carbon-carbon double or triple bond that can be hydrosilylated attaches to one or both, and more preferably both, ends of the siloxane. Preferred groups capable of being hydrosilylated include vinyl moieties, such as 1-propenyl, 1-butenyl, 1-pentenyl, and the like.

In certain preferred embodiments, the redox initiator of Formula (II) can be further defined wherein:
A is 3-vinyl or 3-allyl;
X is hydrogen or Br;
Z is aldehyde, more preferably methanal, or an aldehyde derived from an acetal such as dimethylacetal; and
$R_1$ is phenyl.

Particularly preferred redox initiators include 2-phenyl-4-pentenal, and 2-phenyl-2-bromo-4-pentenal. Particularly preferred redox initiators wherein Z is an aldehyde derived from an acetal include aldehydes derived from 2-phenyl-(1,1'-dimethoxy)-4-pentene or 2-phenyl-2-bromo-(1,1'-dimethoxy)-4-pentene.

Alternatively, these and other aldehydes can be synthesized by methods known in the art. For example, substituted-4-pentenals suitable for the present invention can be synthesized as described in U.S. Pat. No. 3,928,644, wherein 2-phenyl-4-pentenal is synthesized from phenyl acetaldehyde.

After the redox initiator is synthesized, it is attached to a siloxane as described above. In certain preferred embodiments, these redox initiators are terminally attached to the siloxane.

As used herein, the term "siloxane" refers to straight-chain compounds having silicon atoms single-bonded to oxygen atoms and so arranged that each silicon atom is linked to at least one oxygen atom. Preferably, siloxanes of the present invention will be silicones (i.e. siloxane polymers based upon a structure consisting of alternating silicon and oxygen atoms with various organic radicals attached to the silicon atoms). In addition, siloxanes suitable for the present invention have at least one silicon-hydrogen bond which serves as the attachment site for the redox initiator. Thus, preferable siloxanes include hydride end-capped siloxanes. Preferably, siloxanes for use with the present invention will be of the following formula (VII):

(VII)

wherein
$R_7$ is hydrogen;
$R_8$ is independently hydrogen, $C_1$-$C_{50}$ straight or branched alkyl, $C_3$-$C_{12}$ substituted or unsubstituted cyclic, $C_1$-$C_{11}$ heterocyclic, $C_6$-$C_8$ aryl, $C_6$-$C_8$ aryloxy, $C_1$-$C_{12}$ alkoxy, $C_2$-$C_{12}$ di-alkylamino, $C_1$-$C_{12}$ alkylthio, $C_1$-$C_{12}$ fluoroalkyl, $C_1$-$C_{12}$ epoxy, $C_1$-$C_6$ acrylic or methacryoxy, $C_6$-$C_{50}$ polyether, or some combination thereof;
$R_9$ is provided that at least one $R_8$ constituting the $R_9$ is hydrogen; and
p is an integer from 3 to 40.

In certain preferred embodiments, hydride end-capped siloxanes, mono hydride siloxanes, and rake hydride siloxanes have the following formula:

(VIII)

wherein
$R_{16}$ and $R_{17}$ are independently methyl or phenyl, x is an integer from 0-80,
y is an integer from 0-80, and
x+y≠0.

Siloxanes according to the present invention are commercially available from a variety of sources, including for example, dimethylsiloxane-hydrogen terminated (CAS No. 70900-21-9) from Dow Corning, and dimethyl, methylhydrogensiloxane-trimethylsiloxy terminated (CAS No. 68037-59-2) also from Dow Corning.

Alternatively, these and other siloxanes may be prepared by any means known in the art. For example, a polydimethylsiloxane (PDMS) having terminal silicon-hydride functionality may be formed by reacting octamethylcyclotetrasiloxane with dimethyl silane in the presence of $CF_3SO_3H$. A polydimethyl siloxane having pendent silicon-hydride functionality may be formed by reacting octamethylcyclotetrasiloxane and 1,3,5,7-tetramethylcyclotetrasiloxane with tetramethyldisiloxane (TMDS) in the presence of $CF_3SO_3H$.

A preferred method of attaching a redox initiator to the silicon atom is via hydrosilylation. Although not being bound to any particular theory, it is believed that such hydrosilylation reactions occur at a silicon-hydrogen bond of each end of the hydride end-capped siloxane and involve the addition of a siloxane across a carbon-carbon double bond of the redox initiator. Typically, the hydrosilylation process is carried out in the presence of a catalyst, such as a platinum or platinum-based catalyst.

Once the redox initiator is attached to the siloxane, the compound can participate in a redox copolymerization reaction with vinyl monomers or polymers. The term "polymerizable siloxane", as used herein, refers to siloxane polymers having functional group capable of transforming the siloxane compound into a polymeric radical during a copolymerization process. Typically, the polymerization occurs at the alpha-carbon of the redox initiator derivative (i.e., the carbon adjacent to the aldehyde functional group). Thus, according to another aspect of the present invention, provided are novel siloxane polymers having terminal aldehyde functionality.

It is understood that the polymerizable siloxanes mentioned above are merely exemplary and that many other embodiments of the present invention are also contemplated, including but not limited to, cyclic siloxanes, polycyclic siloxanes, and siloxanes having different functional groups attached to the silicon atoms.

According to another aspect of the present invention, methods for preparing block and graft copolymers are provided wherein a polymerizable siloxane, such as those described above, is reacted with a vinyl monomer and/or polymer in the presence of a catalyst to produce a siloxane-vinyl copolymer.

As used herein, the term "vinyl" refers to a moiety having, or being derived from, at least the functional group $CH_2=CH-$. The term "vinyl monomer", as used herein, generally refers to vinyl compounds (i.e. compounds having a vinyl functional group), which includes, but is not limited to vinyl chloride, vinyl acetate and similar esters, styrenes, methacrylates, acrylonitriles, and the like. Preferably, the copolymerization reaction involves the formation of a polymeric siloxane radical which is reacted with a vinyl monomer or polymer to yield the siloxane-vinyl copolymer.

In a particularly preferred embodiment, the copolymerization process includes the step of mixing aldehyde-functional polymerizable siloxanes with a vinyl monomer and a copper (II)redox catalyst system in a suitable solvent such as benzene, toluene, xylene, glycol, or the like, and heated to 60° C.-125° C. for from about 5 to about 24 hours. For preparation of siloxane-polyfluoroolefins, a fluorinated solvent can be used. Once the polymerization reaction is complete, the reaction mixture is cooled to room temperature and mixed with a protic solvent, such as methanol, and the like, to precipitate the copolymer product. The solid product is then washed with a solvent, dried, and purified using typical polymerization techniques known in the art.

The selection of a vinyl monomer for the copolymerization reaction is dependent upon the desired copolymer product. Examples of vinyl monomers that may be used in the present invention include, but are not limited to, ethylene, propylene, styrene, N-vinyl pyrrolidone, vinylidene fluoride, chlorofluoroethylene, methyl methacrylate, ethyl methacrylate, acrylonitrile, hydroxyethyl methacrylate, vinyl acetate, and maleic anhydride. Other examples of vinyl monomers include fluoro olefin monomers such as 3,3,3-trifluoro-1-propene; 2,3,3,3-tetrafluoro-1-propene; 1,3,3,3-tetrafluoro-1-propene; 1-chloro-1,3,3,3-tetrafluoro-1-propene; 2,2,3,3,3-pentafluoro-1-propene; 4-vinyl-pyridine; and the like.

Depending on the starting materials selected for use in the above-described process, a wide range of novel siloxane-vinyl block and graft copolymers can be efficiently obtained. As used herein, the term "block copolymer" refers to a linear copolymer wherein several monomers of a single first species are proximally connected and then sequentially connected to another chain of proximally connected monomers of another single species that is different than the first species. The term "graft copolymer", as used herein, refers to a non-linear copolymer wherein one or more chains consisting of a single species of monomer are connected to a main polymer chain of a different species as side-chains. Thus, according to yet another aspect of the present invention, provided are novel siloxane-vinyl block and graft copolymers.

Additionally, by engineering the redox initiator, the copolymerization reactions which occur are more selective thereby leading to a higher yield and better process control of, and less side products in, the desired product stream. As used herein, the term "product stream" refers to a process wherein siloxane and vinyl monomers are reacted to form a product of block or graft copolymers. Although the term "stream" is used, it should be understood that the present invention can be applied to batch or continuous processes. The term "product yield" refers to the weight percentage of targeted copolymer that is formed via a product stream based upon the weight of the reactants.

EXAMPLES

The present invention is further described in light of the following examples which are intended to be illustrative but not limiting in any manner.

Examples 1-4 demonstrates the preparation of aldehyde functional Silicone-polyethylmethacrylate copolymer.

Example 1

According to this preparation method, a mixture is prepared from the following:
Methacylic acid ethyl ester (55 mL, 50.4 g, 442 mmol)
Dry chlorobenzene (140 mL)
Dry pyridine (7125 µL, 7.0 g)
Triphenylphosphine (4.2 g)
Triethylamine (1932 µL, 1.4 g)
Copper(II)-ethylhexanoate (1.4 g)
Aldehyde Functional Silicone—AFS 11 (3.5 g, 2.55 mmol)
Methanol for used for workup and chlorobenzene was used for washing purposes.

Figure 1:
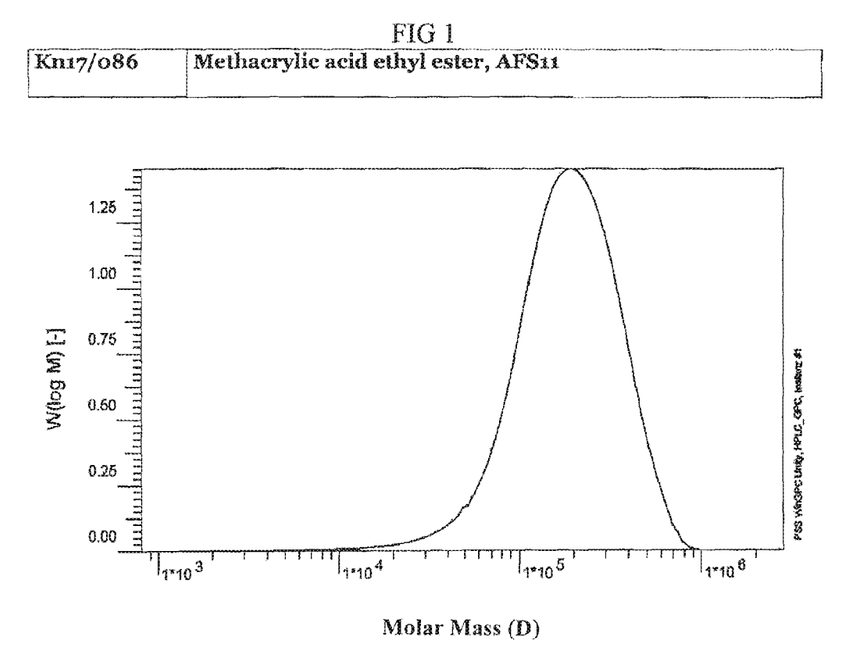
FIG. 1 is a gel permeation chromatography (GPC) scan of the copolymer product of Example 1.

Through the above mentioned mixture a stream of nitrogen is passed for 5 minutes. In an atmosphere of nitrogen, the mixture is heated to 70° C. for 21 hours, during which the reaction mixture becomes viscous. After cooling to approximately 40° C., the solution is transferred to a beaker with an additional 50 mL of chlorobenzene. While stirring with an Ultrturrax machine (IKA Laborwerke), methanol (0.8 L) is added. The polymer precipitates as a rod-like material. More methanol (0.6 L) is added while stirring at high speed (14000 rpm). The mother liquor is decanted off. To the viscous polymeric material more methanol (0.5 L) is added while cooling the beaker with ice. The mixture is stirred for approximately 1 hour. The polymeric material is filtered off, washed with methanol, and then dried with air. The process yields 27.5 g of a white product with some lumps. A GPC scan of this product is shown in FIG. 1.

Example 2

The procedure of Example 1 was repeated, but without chlorobenzene as a solvent and with the following amounts of reactants and reagents:
   5.0 mL Methacrylic acid ethyl ester (4.6 g, 40.2 mmol);
   5.0 mL Catalyst mixture; and
   150 mg AFS03 (0.42 mol %).

Figure 2:
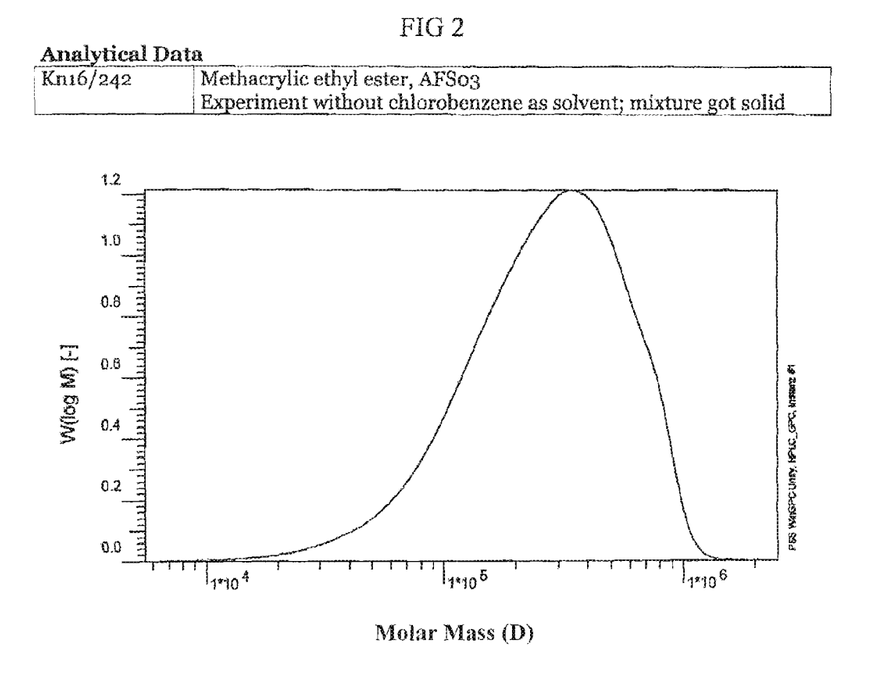
FIG. 2 is a gel permeation chromatography (GPC) scan of the copolymer product of Example 2.

The process yields 3.1 g of isolated product (66%). A GPC scan of this resulting product is shown in FIG. 2.

Example 3

The procedure of Example 1 was repeated, but with the following amounts of reactants and reagents:
   15 mL styrene; and
   1.07 g AFS20.

Figure 3:
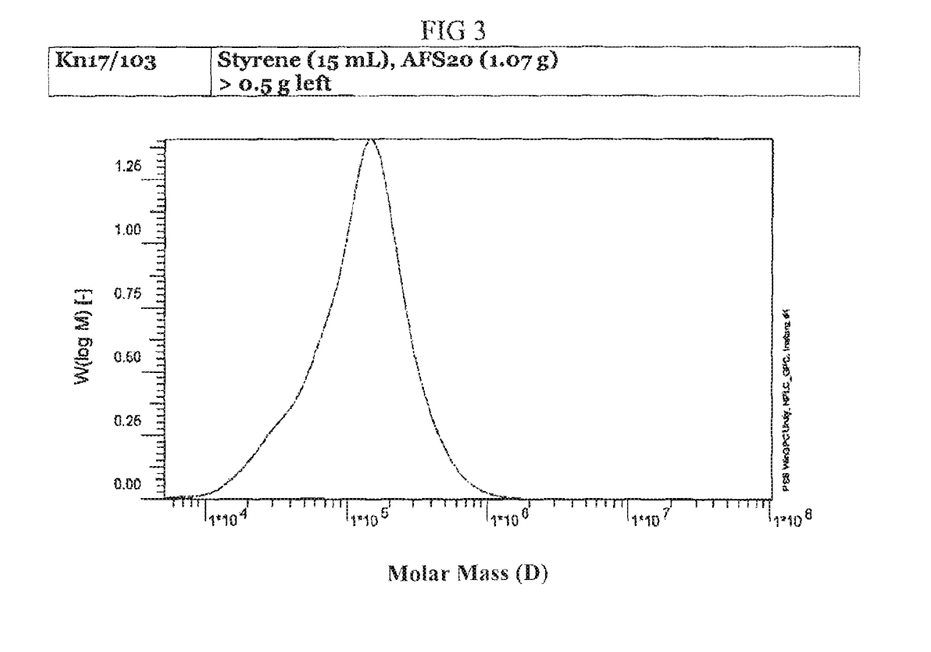
FIG. 3 is a gel permeation chromatography (GPC) scan of the copolymer product of Example 3.

A GPC scan of this resulting product is shown in FIG. 3.

Example 4

The procedure of Example 1 was repeated, but with the following amounts of reactants and reagents:
   10 mL Methacrylic acid ethyl ester (9.17 g, 80.3 mmol);
   3.21 g AFS11 (2.34 mmol);
   20 mL chlorobenzene;
   0.2 g copper(II)-"hexanoate";
   1.0 g pyridine;
   0.6 g triphenylphosphine; and
   0.2 g triethylamine.

Figure 4:
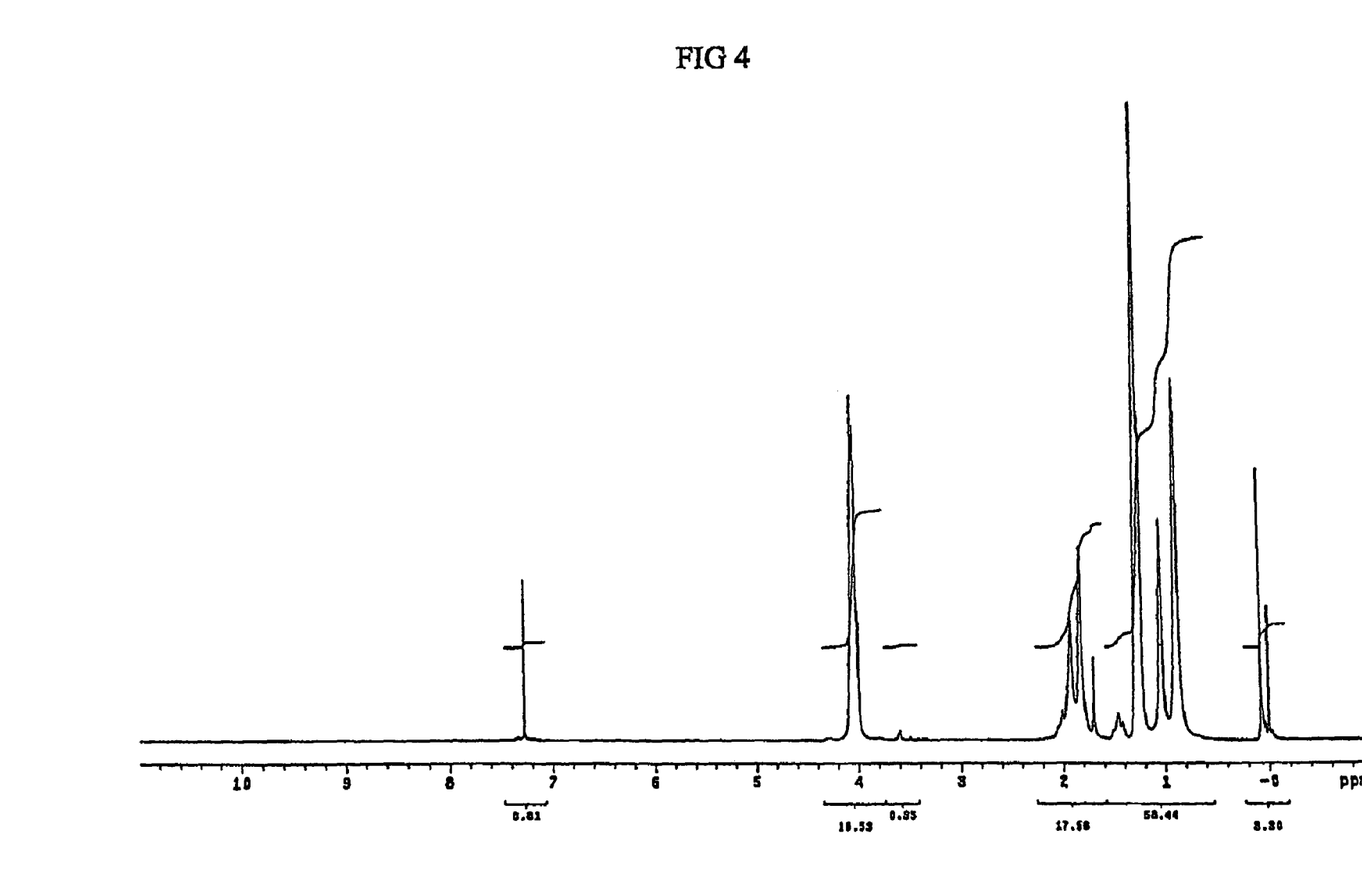
FIG. 4 is an NMR graph of the copolymer product of Example 4.

An NMR scan of the resulting product is shown in FIG. 4.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for preparing a siloxane polymer comprising the steps of:
   (a) providing at least one redox initiator having the formula:

wherein: Z is an aldehyde;
   X is an abstraction moiety selected from the group consisting of hydrogen, chloride, bromide, and iodide;
   $R_1$ is a stabilizing constituent selected from the group consisting of alkyl and aryl; and
   A is a $C_2$-$C_6$ alkene or a $C_2$-$C_6$ alkyne; and
(b) reacting said redox initiator with a hydride end-capped siloxane to form a siloxane polymer having a plurality of terminal aldehyde moieties.

2. The method of claim 1 wherein $R_1$ is selected from the group consisting of phenyl, methyl, and ethyl.

3. The method of claim 2 wherein $R_1$ is phenyl.

4. The method of claim 1 wherein X is hydrogen.

5. The method of claim 1 wherein A is selected from the group consisting of 2-vinyl, 3-allyl, or 4-butenyl.

6. The method of claim 1 wherein said redox initiator is selected from the group consisting of 2-phenyl-4-pentenal and 2-phenyl-2-bromo-4-pentenal.

7. The method of claim 1 wherein said redox initiator has the formula:

wherein x is 1 or 2.

8. The method of claim 1 wherein said siloxane has the formula:

wherein $R_7$ is hydrogen;
   $R_8$ is independently selected from the group consisting of hydrogen, $C_1$-$C_{50}$ straight or branched alkyl, $C_3$-$C_{12}$ substituted or unsubstituted cyclic, $C_1$-$C_{11}$ heterocyclic, $C_6$-$C_8$ aryl, $C_6$-$C_8$ aryloxy, $C_1$-$C_{12}$ alkoxy, $C_2$-$C_{12}$ di-alkylamino, $C_1$-$C_{12}$ alkylthio, $C_1$-$C_{12}$ fluoroalkyl, $C_1$-$C_{12}$ epoxy, $C_1$-$C_6$ acrylic or methacryoxy, $C_6$-$C_{50}$ polyether, or some combination thereof;
   $R_9$ is a moiety having the formula provided that at least one $R_8$ of this moiety is hydrogen; and
p is an integer from 3 to 40.

9. The method of claim 1, wherein said siloxane has a formula of:

wherein $R_{16}$ and $R_{17}$ are independently methyl, ethyl, or phenyl, x is an integer from 0-80, y is an integer from 0-80, and

$x+y \neq 0$.

10. The method of claim 1 wherein said reacting step comprises a hydrosilylation process.

11. The method of claim 10 wherein said hydrosilylation process occurs in the presence of a platinum catalyst.

12. A method of producing a copolymer comprising the steps of:

(a) providing at least one redox initiator having the formula:

wherein: Z is an aldehyde having carboxyl and carbinol functionalities;

X is an abstraction moiety;

$R_1$ is a stabilizing constituent; and

A is a $C_2$-$C_6$ alkene or a $C_2$-$C_6$ alkyne;

(b) reacting said redox initiator with a hydride end-capped siloxane to form a siloxane polymer having a plurality of terminal aldehyde moieties;

(c) providing a monomer or polymer having a vinyl functional group and a second functional group; and

(d) reacting said siloxane polymer with said monomer or polymer to produce a copolymer having aldehyde functionality and said second functionality.

13. The method of claim 12 wherein said vinyl compound is selected from the group consisting of ethylene, propylene, styrene, N-vinyl pryrrolidone, vinylidene fluoride, chloroflouoroethylene, methyl methacrylate, ethyl methacrylate, acrylonitrile, hydroxyethyl methacrylate, vinyl acetate, maleic anhydride, 3,3,3-trifluoro-1-propene, 2,3,3,3-tetrafluoro-1-propene, 1,3,3,3-tetrafluoro-1-propene, 1-chloro-1,3,3,3-tetrafluoro-1-propene, 1,1,3,3,3-pentafluoro-1-propene, and 4-vinyl-pyridine.

14. The method of claim 12 wherein said copolymer is a block copolymer or a graft copolymer.

15. The method of claim 12 wherein said copolymer comprising at least one functionality selected from the group consisting of acrylates, polyolefins, acylate-vinylpyrrolidones, fluorinated organic, and styrenyl.

16. A siloxane polymer comprising a plurality of moieties having the structure:

wherein;

x' is an integer from 2 to 6;

$R_1$ is methyl, ethyl, or phenyl; and $R_8$ is independently selected from the group consisting of hydrogen, $C_1$-$C_{50}$ straight or branched alkyl, $C_3$-$C_{12}$ substituted or unsubstituted cyclic, $C_1$-$C_{11}$ heterocyclic, $C_6$-$C_8$ aryl, $C_6$-$C_8$ aryloxy, $C_1$-$C_{12}$ alkoxy, $C_2$-$C_{12}$ di-alkylamino, $C_1$-$C_{12}$ alkylthio, $C_1$-$C_{12}$ fluoroalkyl, $C_1$-$C_{12}$ epoxy, $C_1$-$C_6$ acrylic or methacryoxy, and $C_6$-$C_{50}$ polyether, or some combination thereof.

17. The polymer of claim 16 wherein $R_1$ is phenyl.

18. The polymer of claim 17 wherein $R_8$ is methyl or phenyl.

19. The polymer of claim 18 wherein $R_8$ is methyl.

20. The polymer of claim 17 wherein X is hydrogen.

21. A personal care product comprising a siloxane polymer of claim 16.

22. The personal care product of claim 21 wherein said siloxane polymer is present in an amount effective to produce a tactile impression.

23. A method of delivering an active ingredient to a bodily surface comprising the step of suspending said active ingredient in a siloxane polymer according to claim 16.

24. The method of claim 23 wherein said suspension step involves carrying or encapsulating said active ingredient in said siloxane polymer.

25. The method of claim 23 wherein said active ingredient is biologically active.

26. The method of claim 23 wherein said active ingredient is cosmetically active.

27. The method of claim 23 wherein said active ingredient is selected from the group consisting of sugars, polysaccharides, proteins, peptides, amino acids, and vitamins.

28. The method of claim 23 wherein said bodily surface is the surface of skin, nail, or hair.

29. A copolymer comprising a siloxane unit having the structure of:

wherein;

x' is an integer from 2 to 6;

$R_1$ is methyl, ethyl, or phenyl; and $R_8$ is independently selected from the group consisting of hydrogen, $C_1$-$C_{50}$ straight or branched alkyl, $C_3$-$C_{12}$ substituted or unsubstituted cyclic, $C_1$-$C_{11}$ heterocyclic, $C_6$-$C_8$ aryl, $C_6$-$C_8$ aryloxy, $C_1$-$C_{12}$ alkoxy, $C_2$-$C_{12}$ di-alkylamino, $C_1$-$C_{12}$ alkylthio, $C_1$-$C_{12}$ fluoroalkyl, $C_1$-$C_{12}$ epoxy, $C_1$-$C_6$ acrylic or methacryoxy, $C_6$-$C_{50}$ polyether, or some combination thereof;

and a second monomer or unit having a different structure.

30. The copolymer of claim 29 wherein said second monomer or unit is selected from the group consisting of sugars, saccharides, and polysaccharides.

31. A personal care product comprising a copolymer of claim 30.

32. The personal care product of claim 31 wherein said copolymer is as a cationic or anionic surfactant, foam control agent, surface modifier, rheology modifier, lubricant, film former, or adhesive.

* * * * *